(12) United States Patent
Bernhardt

(10) Patent No.: US 7,840,380 B2
(45) Date of Patent: Nov. 23, 2010

(54) METHODS AND SYSTEMS FOR PLUME CHARACTERIZATION

(75) Inventor: Roger D. Bernhardt, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 246 days.

(21) Appl. No.: 12/039,947

(22) Filed: Feb. 29, 2008

(65) Prior Publication Data

US 2009/0222207 A1    Sep. 3, 2009

(51) Int. Cl.
*G21C 17/00* (2006.01)
*G01J 1/00* (2006.01)
*G01J 3/10* (2006.01)

(52) U.S. Cl. .................... 702/183; 702/189; 250/494.1; 250/495.1; 250/504 R

(58) Field of Classification Search ................. 702/183, 702/189; 250/494.1, 504 R, 495.1
See application file for complete search history.

(56) References Cited

U.S. PATENT DOCUMENTS

| 4,794,248 | A | * | 12/1988 | Gray ........................... 250/221 |
| 5,648,914 | A | | 7/1997 | Bauer et al. |
| 6,085,152 | A | * | 7/2000 | Doerfel ........................ 702/3 |
| 6,252,689 | B1 | * | 6/2001 | Sharp .......................... 398/168 |
| 6,455,851 | B1 | * | 9/2002 | Lord et al. ............... 250/338.5 |
| 6,809,648 | B1 | | 10/2004 | Fleming |
| 6,997,050 | B2 | | 2/2006 | Fleming |
| 7,071,466 | B2 | | 7/2006 | Glukhoy |
| 7,102,514 | B2 | | 9/2006 | Berry |
| 2004/0047776 | A1 | | 3/2004 | Thomsen |
| 2006/0023211 | A1 | | 2/2006 | Gandhi et al. |
| 2007/0090942 | A1 | | 4/2007 | Berry |

OTHER PUBLICATIONS

United States Statutory Invention Registration No. US H2208H; Published Jan. 1, 2008; Inventor: Stytz, et al.

* cited by examiner

*Primary Examiner*—Jeffrey R West
*Assistant Examiner*—Janet L Suglo
(74) *Attorney, Agent, or Firm*—Armstrong Teasdale LLP

(57) ABSTRACT

A method for mapping, in three dimensions, the contents of a plume within an area is described. The method includes distributing spectrally sensitive sensors on a first surface of a vehicle, distributing spectrally sensitive emitters on a second surface of a vehicle, causing the emitters to output a signal directed through the plume and towards the sensors, receiving at least a portion of the emitter output at the sensors, communicating an output of the sensors, the sensor output caused by the received optical emitter output, to a central processing unit, and analyzing the sensor outputs and time-based vehicle positions to characterize the plume and an area surrounding the plume in three dimensions over a period of time.

20 Claims, 2 Drawing Sheets

METHODS AND SYSTEMS FOR PLUME CHARACTERIZATION

BACKGROUND OF THE INVENTION

This invention relates to characterizing a threat plume or threat cloud, identifying components disbursed within the atmosphere due to the plume, and more specifically, to methods and systems for characterizing the shape, size, and constituent components present in a plume.

A plume is herein defined as a sub-volume of space in air, or water containing constituents, for example, pollutants or other agents, that are found in the greater fluid volume. Currently, plume characterization and constituent component identification, for example within an airborne plume is accomplished through remote optical methods or through the utilization of an unmanned aerial vehicle (UAV) equipped with a plurality of complex sensors. However, these solutions provide a limited capability in that they cannot accurately and rapidly map a plume in three dimensions. More specifically, the above mentioned current solutions provide a limited capability to accurately and rapidly map, in three dimensions, all of the size, shape and density characteristics and component constituents of an airborne plume.

BRIEF DESCRIPTION OF THE INVENTION

In one aspect, a method for mapping, in three dimensions, the contents of a plume within an area is provided. The method includes distributing spectrally sensitive sensors on a first surface of a vehicle, distributing spectrally sensitive emitters on a second surface of a vehicle, causing the emitters to output a signal through the plume and towards the sensors, receiving at least a portion of the emitter output at the sensors, communicating an output of the sensors, the sensor output caused by the received emitter output, to a processing unit, and analyzing the sensor outputs and time-based vehicle positions to characterize the plume and an area surrounding the plume in three dimensions over a period of time.

In another aspect, a system is provided for the mapping of the contents of a plume within an area, where the mapping is in three dimensions. The system includes a transmitter node: comprising a processing device, a plurality of emitters, and a network communication link; a receiver node: comprising a processing device, a plurality of sensors configured to detect emissions from the emitters, and a network communication link; a communication network communicatively coupled to the transmitter node and to the receiver node via the network communication links; and a network manager operating via the communication network and configured to distribute processing among the nodes, provide emitter and sensor directional control, and provide node position control.

DETAILED DESCRIPTION OF THE INVENTION

The methods and systems described herein relate to the mapping and characterizing, in three dimensions, the contents of a plume. A plume may be airborne, dispersed within or along the ground, or dispersed underwater. In the airborne case, optical characteristics associated with the contents of the plume are determined utilizing multiple unmanned aerial vehicles (UAVs) configured with cooperative emitters and detectors. These cooperative emitters and detectors provide, and include, detection and characterization of inter vehicular emissions paths and intra vehicular emissions paths.

To provide such emissions paths, the UAVs include one or more of smart sensor body coatings, simple reflectors, simple and complex spectroscopic emitters, and sensor fusion processing capabilities. The embodiments, as further described herein, allow users to map and characterize the component and/or constituent contents of a plume, cloud, or other particle mass in an open atmosphere or other body of fluid (air or water) using cooperative sensors. Such embodiments may further provide for the identification of the component and constituent makeup of the plume being examined.

Figure 1:
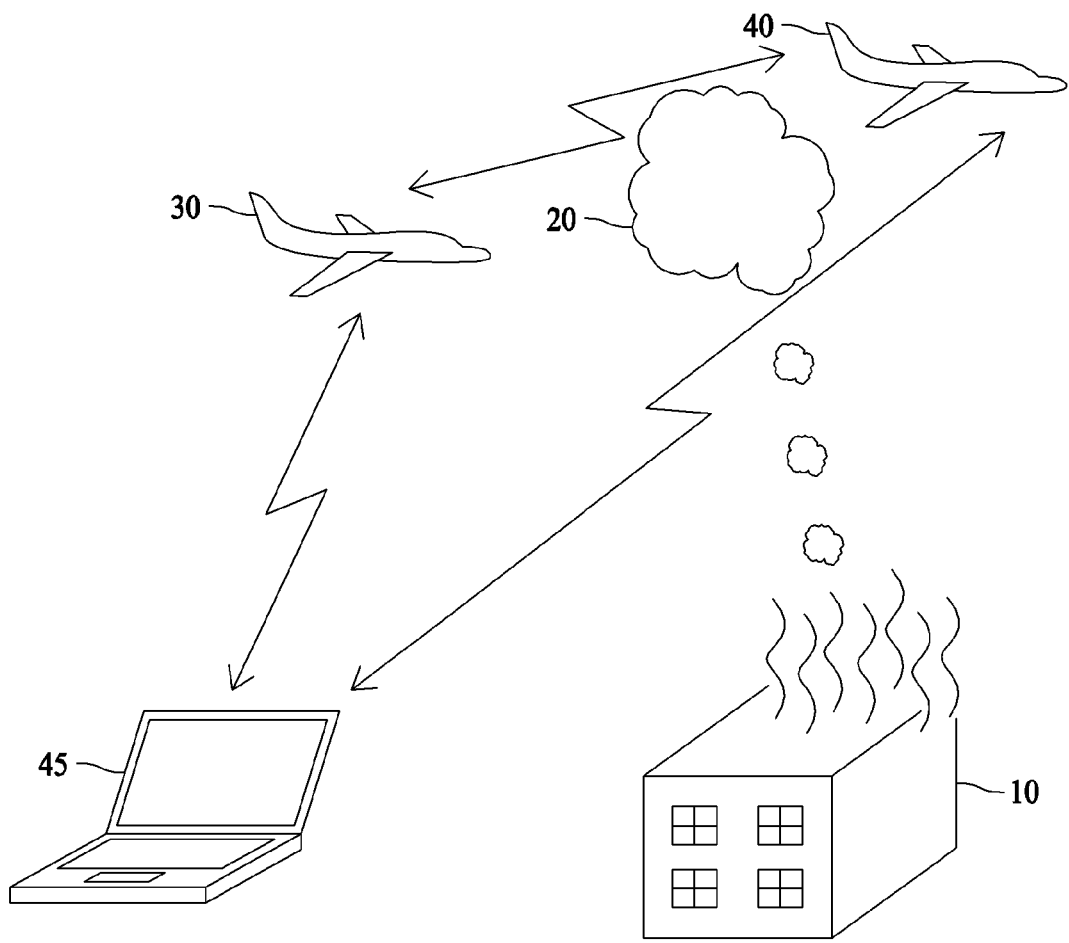
FIG. 1 is an illustration of an airborne plume and two unmanned aerial vehicles configured with cooperative emitters and detectors for the testing and identification of plume contents.

FIG. 1 is an illustration of one embodiment of plume mapping. Specifically, FIG. 1 includes a depiction of a building 10 that has been hit by a bomb. As a consequence of the bomb blast, an airborne plume 20 has occurred. The airborne plume 20 may include constituents from the bomb or explosive damage itself, but may also contain constituents from items that were stored within the building 10. In one currently relevant example, the building 10 may have been bombed because it was suspected that chemicals or compounds related to a biological hazard or threat were being stored or produced within the building 10. If true, and such chemicals and components were in building 10 as the bomb exploded, components of these chemicals and compounds might be found in the plume 20.

In FIG. 1, a first UAV 30 operates as a transmitter, in one embodiment, utilizing a pulsed multi-spectral LED array, and a second UAV 40 operates as a receiver, in one embodiment, utilizing any or all of ultra-violet/electro-optical/infrared (UV/EO/IR) cameras in arrays that collect the emissions from the activated elements of the array that pass through the plume 20.

Such emitter and detector configurations profiles a volume of fluid more accurately and rapidly than the currently utilized monitoring systems. Through the cooperative and separate transmitters and receivers, a dual mode, real time sensing and distributed networking capability is added to a platform. Referred to elsewhere as a network centric operation (NCO) sensor system, such a system provides a capacity for real time chemical and biological agent mission capabilities.

As mentioned above, one embodiment of the NCO sensor system utilizes a pulsed, multi-spectral, LED array transmitter, and receives spectral information as the output of the LED array is collected by EO/IR cameras on one or more receivers to provide real time identification, surveillance, reconnaissance and data transformation. When provided, for example, on separate UAVs, the transmitter and the receiver offer a large field of view with minimal or no pointing of the transmitter and receiver to provide a baseline capability.

Two UAVs working together require less power to rapidly and accurately map a dispersion associated with a plume in three dimensional space using NCO distributed processing than reflective sensing approaches such as lidar or radar systems. This distributed processing disperses the work load supporting these enhanced sensor techniques through a connection to an atmospheric analysis measurement network (AAMN) 45. In one embodiment, the receiver (UAV 40) autonomously controls flight profiles of the associated UAV, communicates data associated with an analysis of a plume between the UAVs, and communicates the analysis data to a remote base of operations via AAMN 45. The resulting distributed network-enabled sensing enhances mission operational effectiveness.

While described herein with respect to a two UAV system, systems that utilize more than two UAVS, each configured as one or both of a transmitter and receiver are contemplated. Additionally, systems that utilize a single UAV, with one portion of the UAV configured as a transmitter while another portion of the UAV is configured as a receiver are contemplated. One such example is a UAV where one wingtip is a transmitter and the other wingtip is a receiver. Further, a system with a wingtip transmitter and an aircraft body receiver configuration and a system with a wingtip receiver and an aircraft body transmitter configuration may be deployed. Any of the above described configurations are capable of rapidly mapping a plume in three dimensions. Manned platforms, though at risk while operating in a risk environment, also benefit from incorporation of the described embodiments.

In addition, coating a UAV or parts thereof with smart sensors and/or active emitters of various spectral range creates a powerful, multi-mode, sensing system. Remote sensing of such smart elements can extend to ground interrogation and cooperation all the way to space and seaborne systems. Rather than limiting the embodiments to UAVS, underwater applications are contemplated. In one embodiment, buoys, hulls, submersibles, and the like that incorporate the transmitting and receiving capabilities such as those described with respect to airborne plume monitoring are possible. Further, applications where commercial aircraft are utilized as sensors of their environment are contemplated as well as applications where cars, trucks, other vehicles, and even stationary structures are capable of utilization in three dimensional atmospheric monitoring applications.

Utilizing the above described NCO configuration, a bomb damage plume is mapped for location, shape, and size. In some cases, potential threat agents, particulates, and/or aerosols, as well as any other constituents of interest therein are identified, where practical, through one or more of optical, ultraviolet, and infrared measurements using multiple UAVs. The approach utilizes simple pulsed differential absorption, comparing the ratio of absorption between different wavelengths to the known absorption profile of clear air. In addition, reflective and scattering measurements, a so-called "bloom" from any reflections caused by the plume provides another sensing mechanism.

In one embodiment, a transmitter is located on the first (emitter) UAV 30 and the second (receiver) UAV 40 is configured as a sensor receiver due to the incorporation of enhanced electro-optic, ultraviolet, and/or infrared surveillance sensors. To achieve plume tracking, the network processing capability associated with the NCO sensor system provides: sensor tracking, enhanced relative position, reflection "bloom" calculations, command and control functions, three dimensional mapping, self-calibration and test, data fusion, and network management.

By operating as a network node, the two UAVs 30 and 40 act as a single unit resulting in a cooperative three dimensional sensor system. While older systems often require heavy and high power lasers to create diffuse scattering of particles or aerosols for making measurements, the network centric sensor systems described herein require much less power, especially when compared to standoff reflectance techniques used by LIDAR systems.

The system architecture for the NCO sensor system reduces sensor size, weight, and power requirements by creating a sensor fabric to enable distributed sensors for real time mapping and tracking of a threat plume. As further described, a network manager (NM) controls processing, provides emitter and sensor directional processing, and vehicle (node position) control and analytical processing.

The benefits of such a system configuration include: one way propagation that limits the required transmission power, a wide field of view sensor is simple and lightweight to minimize or eliminate pointing, control and synchronization through NCO computing increases mission capabilities by sharing processing workloads, mature distributed sensor hardware provides a low risk solution, and additional network and processing capabilities enable enhancements that include using local ultraviolet fluorescence flash microscopy, and threat agent sensitive optical coatings that change characteristics in the presence of various threats.

Figure 2:
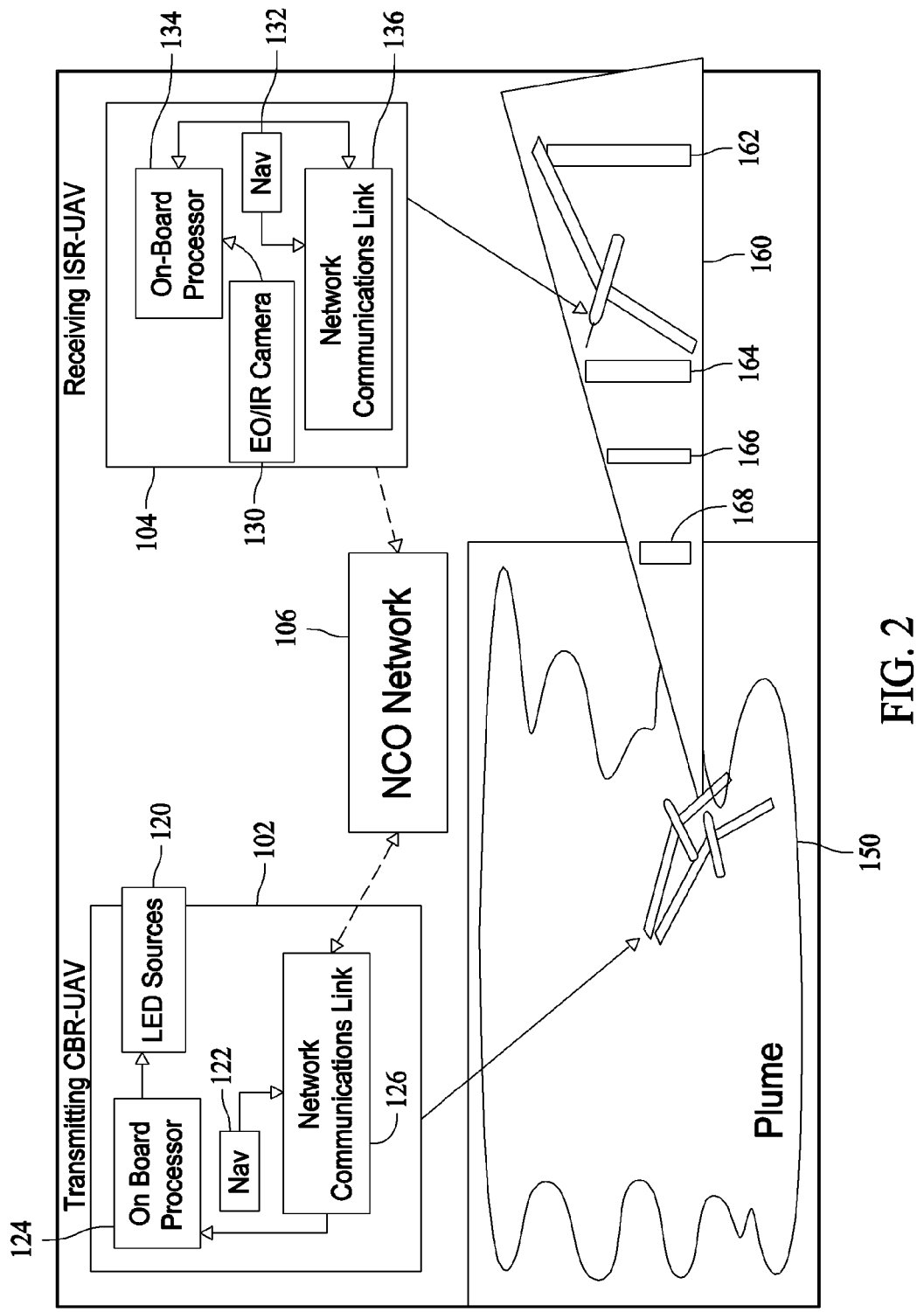
FIG. 2 is a functional block diagram of a distributed sensor system configured for the detection of particulates, aerosols and/or vapors within a plume.

FIG. 2 is a functional block diagram of one embodiment of a distributed sensor system 100 configured for the detection of particulates, for example in an airborne plume. The architecture of system 100 includes three elements: a transmitter node 102, a receiver node 104, and a communication network 106 that provides network centric operation and which includes a connection to the atmospheric analysis measurement network (AAMN) 45 (shown in FIG. 1).

The transmitter node 102 includes a multi-spectral illumination source, illustrated as LEDs 120, a navigational/GPS system 122, an on board processor 124, and a network communication link 126. The processor 124 provides control for the LEDs 120 and receives data via the network communication link 126. The navigational/GPS system 122 provides data to the network communication link 126 which in turn communicates with the communication network 106. In one embodiment, the number of transmitting devices (e.g., LEDs 120) is optimized for measurement sensitivity and plume characterization at ranges between 50 to 1000 meters.

In this embodiment, the receiver node 104 includes an electro-optic/infrared (EO/IR) camera 130, a navigational/GPS system 132, an on board processor 134, and a network communication link 136. The GPS system 132 and processor 134 provide data for the camera pointing angles 130 and receives data via the network communication link regarding the location of the emitters position in the field of view 136. In one embodiment, efficient low power sources, e.g., the LEDs 120 are easily detected as the EO/IR camera 130 is sensing unidirectional emissions, for example, at less than 500 meters. Diminished visibility infers plume density so loss of signal is an intended consequence of the sensing mode.

Peer to peer (P2P) communication is used to link the transmitter node 102 and receiver node 104 platforms to provide seamless flow of information between the nodes 102 and 104 and throughout the network 106 creating an NCO environment. This type of configuration enables real time distributed node control/track data and analytical processing using an NCO sensor fabric technology. More specifically, a network manager (NM) schedules the sensor resources by controlling the onboard network processing, communications, EO and near IR cameras, and flight control functions of multiple vehicles, for example nodes 102 and 104. In one embodiment, the NM acts as a super-node on the transmitter node 102, controlling the output of the LEDs 120 and the communication of information sent to the receiver node 104.

The EO/IR cameras 130 detect the multi-spectral emissions from the transmitter 102, as provided via the LEDs 120 through plume 150. The receiver 104 incorporates distributed real time processing within the on-board processor 134 then measures the intensities of the absorption and scattering of the received light from the LEDs 120 to map the plume 150.

The onboard processor 134 additionally tracks the transmitting platform (transmitter node 102) while also measuring intensities of the different transmitter wavelengths from the appropriate pixels of the image to develop the desired three dimensional image of the plume in real time. In one embodiment, the transmitter node 102 sends a calibration sequence on initial deployment that intermittently illuminates different LEDs, emitting at various wavelengths, to determine background levels and system noise that might be sensed by the receiver node 104. One embodiment of a calibration sequence 160 is depicted in FIG. 2. Sequence 160 includes sequences components 162, 164, 166, and 168 which represent illumination of different LEDs of different wavelengths.

Real time data fusion takes place on the receiver node 104 which significantly reduces the latency and bandwidth limitations imposed by centralized architectures. Specifically, the processing load is distributed across multiple nodes (not shown) of the networked system 100 by the distributed NM for optimal use of the limited electrical and processing power available on the individual UAVs. Reconfiguration of the adaptable, distributed processing capabilities allows the sensor, processing and security hardware to perform real time sensor data analysis and fusion while coordinating avionic functions (flight control, communications, sensor/emitter coordination, etc.) on the UAV platforms. The NM maps out the flight profiles of transmitter nodes, such as node 102, and receiver nodes, such as node 104, to ensure adequate coverage of the suspected plume region. Orientation and sensor (cameras) pointing data associated with the receiver nodes are developed from algorithms processing real time data to optimize gathered data and information.

Additionally, the distributed NM combines the multi-spectral intensity measurements, controls (modulates) the transmitter power and spectrum adaptively to help identify and map a plume. The NM then creates a three dimensional map of the plume and characterizes its contents. The relative absorption of the different wavelengths received from the multi-spectral illuminator of transmitter node 102 allows the contents of the plume 150 to be characterized.

In one application scenario, when the plume is to be generated from a forthcoming tactical or strategic strike, the UAV associated with the transmitter node 102 is positioned downwind and downrange of the planned bomb strike. Upon receiving notification that a strike has occurred, this UAV approaches a suspected plume region and begins a search pattern. The UAV associated with the receiver node 104 then begins a flight profile based on observing the search pattern associated with the transmitter node 102.

Information from both the transmitter node 102 and the receiver node 104 is processed by a distributed data fusion node via the network communication links of the platforms and the information is processed. Once a measurable concentration of particulates is detected, the NM optimizes the plume mapping and characterization by adaptively modifying the UAV flight profiles associated with the transmitting and receiver nodes 102 and 104 and further operates to log the directions that the selected LEDs 120 and the selected EO/IR cameras 130 are pointed. This decreases the overall mission timeline for sampling.

In an embodiment where all UAV's carry emitter arrays and sensor receivers on the same platform additional dual role capabilities are afforded to the mission profile. For example, the receiver node 104 can perform additional missions associated with operation of the network 106, including reconnaissance and communications relay functions. In an alternative embodiment, an additional platform may be deployed (an additional UAV incorporating one or both of a transmitter and receiver function) to provide enhanced monitoring and further accelerated plume mapping.

In regard to operation of system 100, three areas, sensing, algorithm development and improvement, and sensor fabric are utilized to quantify the benefits of the described NCO sensor system 100 which include improved associated plume tracking algorithms and hyper-spectral real-time sensing to improve chemical sensing using alternate sensing bands. In these cases, active emitters in alternate spectral regions may provide enhanced signatures of vaporous chemical contaminants.

With regard to sensing, real-time, high frame rate, imaging interferometry using the LEDs 120 and the EO/IR cameras 130 improve plume centroid location accuracy. In addition, tunable emitters such as mid-wave infrared (MWIR) laser, photo-acoustic emitters, thermal recycler arrays or other appropriate sources can replace or supplement the baseline multi-spectral illumination sources (e.g., the LEDs 120).

With regard to algorithm development, mapping algorithms on distributed network centric platforms are utilized to more quickly locate and accurately report the position of the plume centroid. LED pulse duration and sequencing algorithms are also utilized to encode data through which chemical and biological agents are identified due to their distinct interactive modalities. Additionally, scan speed, spatial resolution, and spectral resolution are adjustable to provide improved results. Distributed NCO nano-sensors may be utilized in conjunction with the LEDs 120 and other emitters to improve detection and identification.

Utilizing the above described systems and methods, users are able to create "arcs" and "surfaces" of situation awareness about the nature of a propagating plume of material to include information such as a concentration of plume constituents in three dimensions, identification of plume constituents in three dimensions, time correlated propagation data for the plume, and the extents or limits of the plume. The plane surfaces that are formed by the relative motion of the moving lines between cooperating platforms offers a time sequenced characterization capability. Fixed laser diodes provide yet another alternative for long reach mapping as well, again painting plane surface (scattered emission) images onto an evolving map over time as the plume evolves.

While the invention has been described in terms of various specific embodiments, those skilled in the art will recognize that the invention can be practiced with modification within the spirit and scope of the claims.

What is claimed is:

1. A method for mapping in three dimensions the contents of a plume within an area, said method comprising:
distributing spectrally sensitive sensors on a first surface of a vehicle;
distributing spectrally sensitive emitters on a second surface of a vehicle;
causing the emitters to output a signal directed through the plume and towards the sensors;
receiving at least a portion of the emitter output at the sensors;
communicating an output of the sensors, the sensor output caused by the received optical emitter output, to a central processing unit; and
analyzing the sensor outputs and time-based vehicle positions, using the central processing unit, to characterize the plume and an area surrounding the plume in three dimensions over a period of time.

2. A method according to claim 1 wherein distributing optical emitters on a second surface of a vehicle comprises distributing the sensors on a vehicle that is separate from a vehicle on which the emitters are distributed.

3. A method according to claim 2 wherein the separate vehicles are unmanned aerial vehicles.

4. A method according to claim 1 wherein:
distributing sensors comprises distributing the sensor at a first portion of a vehicle; and
distributing emitters comprises distributing emitters at a second portion of the same vehicle, the second portion a distance from the first portion.

5. A method according to claim 1 wherein causing the emitters to output a signal comprises outputting a pulse pattern utilizing a multiple spectrum LED array.

6. A method according to claim 1 wherein receiving at least a portion of the optical emitter output comprises utilizing at least one of electro-optical, ultraviolet, and infrared cameras to collect light from the optical emitters that passes through the plume.

7. A method according to claim 1 wherein analyzing the sensor outputs comprises dispersing at least a portion of the processing associated with analyzing the sensor outputs to a atmospheric analysis and measurement network.

8. A method according to claim 1 wherein analyzing the sensor outputs comprises identifying any threat agents and particulates within the plume through at least one of electro-optical and infrared absorption measurements and electro-optical and infrared scattering measurements.

9. A method according to claim 1 further comprising operating the emitters such that a calibration sequence is output by the emitters and received by the sensors for the purpose of reducing effects of any background noise that might be sensed by the sensors.

10. A method according to claim 1 further comprising adaptively modifying travel profiles of the vehicles associated with the emitters and sensors upon detecting a measurable concentration of a particulate of interest within the plume.

11. A system for mapping contents of a plume within an area, the mapping in three dimensions, said system comprising:
a transmitter node comprising a processing device, a plurality of emitters, and a network communication link;
a receiver node comprising a processing device, a plurality of sensors configured to detect emissions from said emitters, and a network communication link;
a communication network communicatively coupled to said transmitter node and to said receiver node via said network communication links; and
a network manager operating via said communication network and configured to distribute processing among said nodes, provide emitter and sensor directional control, and provide node position control, said network manager further configured to control an output of said emitters and communication of information sent to said receiver node.

12. A system according to claim 11 wherein said plurality of emitters comprises a multiple spectrum illumination source.

13. A system according to claim 11 wherein said plurality of emitters are configured for measurement sensitivity and plume characterization at ranges between about 50 meters and about 1000 meters.

14. A system according to claim 11 wherein said plurality of sensors comprises at least one of electro-optic, ultraviolet, and infrared cameras.

15. A system according to claim 11 wherein said transmitter node and said receiver node each comprise at least one unmanned aerial vehicle.

16. A system according to claim 11 wherein said communication network incorporates peer to peer communication to link said transmitter node and said receiver node.

17. A system according to claim 11 wherein to provide node position control, said transmitter node and said receiver node each comprise an unmanned aerial vehicle comprising at least one of a navigational system and a GPS system.

18. A system according to claim 11 wherein said processing device of receiving node is configured to utilize outputs from said optical sensors to measure intensities of absorption and scattering of different wavelengths of received light from said optical emitters to map characteristics and contents of a plume and an area of the atmosphere surrounding the plume.

19. A system according to claim 11 wherein said transmitter node and said receiver node each comprise an unmanned vehicle, wherein to provide node position control, said network manager is configured to adaptively modify said unmanned vehicle movement profiles associated with said transmitter and receiver nodes to ensure adequate coverage of a region associated with the plume.

20. A system according to claim 11 wherein said transmitter node and said receiver node comprise multiple vehicles within an area.

* * * * *